(12) United States Patent
Ryu et al.

(10) Patent No.: US 9,696,398 B2
(45) Date of Patent: Jul. 4, 2017

(54) MAGNETIC RESONANCE IMAGING AND POSITRON EMISSION TOMOGRAPHY SYSTEM

(71) Applicant: Samsung Electronics Co., Ltd., Suwon-si (KR)

(72) Inventors: Yeun-chul Ryu, Hwaseong-si (KR); Tae-yong Song, Hwaseong-si (KR); Young-beom Kim, Yongin-si (KR); Jae-mock Yi, Hwaseong-si (KR); Seong-deok Lee, Seongnam-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 553 days.

(21) Appl. No.: 14/071,831

(22) Filed: Nov. 5, 2013

(65) Prior Publication Data
US 2014/0221814 A1 Aug. 7, 2014

(30) Foreign Application Priority Data

Feb. 4, 2013 (KR) .................. 10-2013-0012604

(51) Int. Cl.
*G01R 33/48* (2006.01)
*A61B 6/00* (2006.01)
*A61B 6/03* (2006.01)

(52) U.S. Cl.
CPC .......... *G01R 33/481* (2013.01); *A61B 6/4417* (2013.01); *A61B 6/5247* (2013.01); *G01R 33/4808* (2013.01); *A61B 6/037* (2013.01)

(58) Field of Classification Search
CPC ....... A61B 5/0035; A61B 5/055; A61B 6/037; A61B 6/4417; A61B 6/5247; G01R 33/481; G01R 33/4808
See application file for complete search history.

(56) References Cited

U.S. PATENT DOCUMENTS

| 4,722,056 A | 1/1988 | Roberts et al. |
| 4,945,478 A | 7/1990 | Merickel et al. |
| 6,711,429 B1 | 3/2004 | Gilboa et al. |
| 7,092,748 B2 | 8/2006 | Valdes Sosa et al. |
| 7,323,874 B2 | 1/2008 | Krieg et al. |
| 7,728,590 B2 * | 6/2010 | Eberler .................. A61B 5/055 324/318 |
| 8,131,340 B2 * | 3/2012 | Eberlein .......... G01R 33/34046 600/407 |

(Continued)

FOREIGN PATENT DOCUMENTS

| JP | 2012-152551 | 8/2012 |
| KR | 10-0891057 | 3/2009 |

(Continued)

OTHER PUBLICATIONS

Zaidi, Habib, and Alberto Del Guerra. "An outlook on future design of hybrid PET/MRI systems." *Medical physics* vol. 38, No. 10 (Oct. 2011): pp. 5667-5689.

*Primary Examiner* — Long V Le
*Assistant Examiner* — Angela M Hoffa
(74) *Attorney, Agent, or Firm* — NSIP Law

(57) ABSTRACT

Provided is a magnetic resonance imaging and positron emission tomography (MRI-PET) system. The MRI-PET system includes a PET unit and a radiofrequency (RF) coil disposed within a gradient coil assembly.

14 Claims, 6 Drawing Sheets

(56) References Cited

U.S. PATENT DOCUMENTS

| | | | | |
|---|---|---|---|---|
| 8,525,116 | B2* | 9/2013 | Schulz | G01T 1/1603 250/363.02 |
| 8,816,686 | B2* | 8/2014 | Park | A61B 5/0035 324/318 |
| 9,041,397 | B2* | 5/2015 | McBroom | G01R 33/34076 324/307 |
| 9,188,651 | B2* | 11/2015 | McBroom | G01R 33/34076 |
| 9,510,797 | B2* | 12/2016 | Yamaya | A61B 5/055 |
| 2005/0096589 | A1 | 5/2005 | Shachar | |
| 2007/0102641 | A1 | 5/2007 | Schmand et al. | |
| 2009/0206836 | A1* | 8/2009 | Eberler | A61B 5/055 324/307 |
| 2010/0010337 | A1 | 1/2010 | Hagen et al. | |
| 2010/0033186 | A1 | 2/2010 | Overweg et al. | |
| 2010/0036237 | A1* | 2/2010 | Eberlein | G01R 33/34046 600/411 |
| 2010/0056899 | A1* | 3/2010 | Toddes | A01K 1/0613 600/411 |
| 2010/0074501 | A1 | 3/2010 | Ladebeck et al. | |
| 2011/0288401 | A1 | 11/2011 | Solf et al. | |
| 2012/0223715 | A1* | 9/2012 | Park | A61B 5/0035 324/318 |
| 2012/0330128 | A1* | 12/2012 | Park | A61B 6/037 600/411 |
| 2014/0210465 | A1* | 7/2014 | Kim | G01R 33/3635 324/309 |
| 2014/0218033 | A1* | 8/2014 | Ryu | G01R 33/34046 324/319 |
| 2014/0232392 | A1* | 8/2014 | Ryu | G01R 33/5659 324/308 |

FOREIGN PATENT DOCUMENTS

| | | |
|---|---|---|
| KR | 10-1100844 | 1/2012 |
| KR | 10-2012-0022356 | 3/2012 |

* cited by examiner

MAGNETIC RESONANCE IMAGING AND POSITRON EMISSION TOMOGRAPHY SYSTEM

CROSS-REFERENCE TO RELATED APPLICATION

This application claims the benefit under 35 USC §119(a) of Korean Patent Application No. 10-2013-0012604, filed on Feb. 4, 2013, in the Korean Intellectual Property Office, the entire disclosure of which is incorporated herein by reference for all purposes.

BACKGROUND

1. Field

The present disclosure relates to magnetic resonance imaging (MRI)-positron emission tomography (PET) systems including an MRI unit and a PET unit.

2. Description of Related Art

Different types of medical equipment are being used to diagnose abnormalities in the human body. Some examples of such equipments are magnetic resonance imaging (MRI) devices, magnetic resonance spectroscopy (MRS) devices based on the phenomenon of nuclear magnetic resonance (NMR), and positron emission tomography (PET) devices using radioactive isotopes that emit positrons.

An MRI device includes components for applying a radio frequency (RF) signal to a biological tissue of interest so as to induce magnetic resonance from the tissue and for applying a gradient signal to a biological tissue of interest so as to obtain spatial information about the biological tissue. The MRI device may be used to obtain images of internal body structures and distinguish abnormal cells or tissues from normal ones. A PET device produces images of the body by injecting radioactive isotopes which emit positrons and detect gamma rays emitted in the human body. The PET device may be used to obtain information about various biochemical phenomena within parts of the body in which metabolic activities take place.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In one general aspect, there is provided a magnetic resonance imaging and positron emission tomography (MRI-PET) apparatus including a magnet configured to generate a static magnetic field; a coil assembly configured to produce a gradient magnetic field, the coil assembly being disposed inside the magnet; a PET element disposed inside the coil assembly; and radio-frequency (RF) coils disposed at both sides of the PET element and inside the gradient coil assembly.

Each RF coil may include a plurality of loop coils.

The RF coil may include a cylindrical element, and the loop coils may be disposed on a surface of the cylindrical element.

The RF coil may include a plurality of plate coils having a strip line shape.

RF shields may be disposed between the RF coils and the PET unit.

The PET element may include a PET detector.

A bore may be formed inside the PET element and the RF Coils.

In another general aspect, there is provided a magnetic resonance imaging and positron emission tomography (MRI-PET) apparatus including a magnet configured to generate a static magnetic field; a coil assembly configured to produce a gradient magnetic field, the coil assembly being disposed inside the magnet; and a ring structure surrounding a bore formed inside the coil assembly, the ring structure including radiofrequency (RF) coils and PET elements arranged alternately with each other.

RF shields may be disposed between the RF coils and the PET units.

In another general aspect, there is provided a magnetic resonance imaging and positron emission tomography (MRI-PET) apparatus including a magnet configured to generate a static magnetic field; a coil assembly configured to produce a gradient magnetic field, the coil assembly being disposed inside the magnet; a bore formed in the coil assembly; and at least one PET element and at least one radio-frequency (RF) coil disposed in the bore.

The PET element may be disposed along a circumference of the bore and the RF coils may be disposed on both sides of the PET element.

The plurality of PET element and the plurality of RF coils may be ring-shaped and may be alternately disposed along a circumference of the bore.

The plurality of PET element and the plurality of RF coils may be disposed along a cylindrical surface to form a plurality of ring-shaped element; and the ring-shaped elements may be disposed along a circumference of the bore.

A radio-frequency (RF) shield may be disposed between the at least one PET element and the at least one RF coil.

Each RF coil may include a plurality of loop coils disposed on a cylindrical surface of the RF coil.

The plurality of loop coils may not overlap each other.

The plurality of loop coils may overlap each other.

A plurality of insulators may separate the loop coils from each other.

The RF coil may include a plurality of plate coils disposed on a cylindrical surface of the RF coil.

The plurality of plate coils may be arranged uniformly along the centerline of the cylindrical surface of the RF coil.

The plurality of plate coils may be arranged in a staggered pattern along the centerline of the cylindrical surface of the RF coil.

Other features and aspects will be apparent from the following detailed description, the drawings, and the claims.

Figure 1:
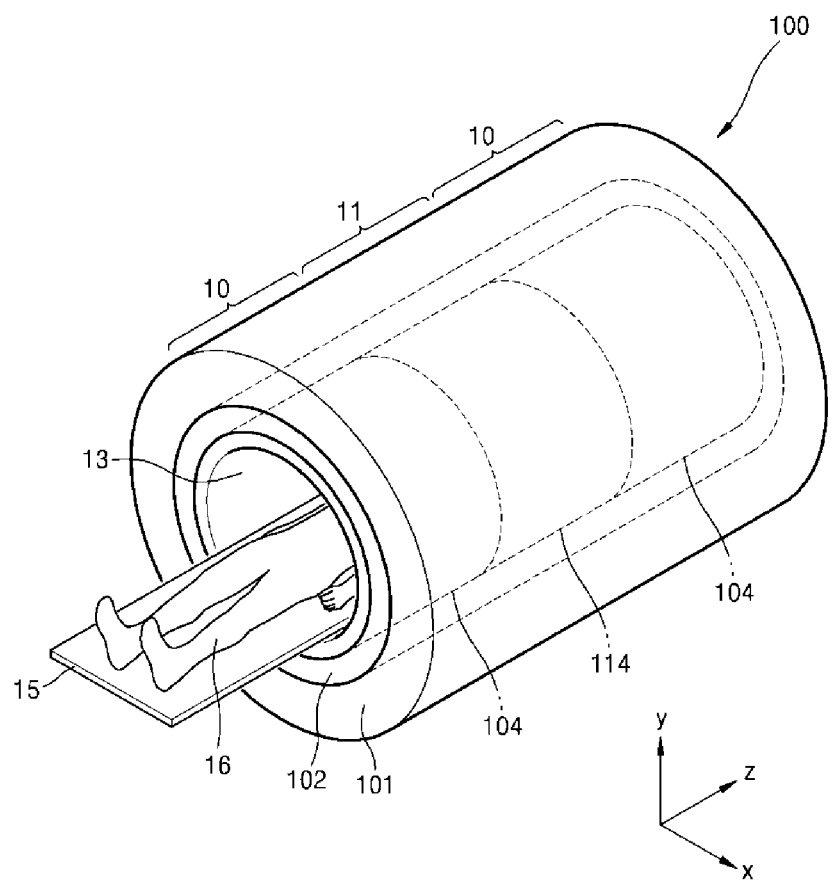
FIG. 1 illustrates an example of a magnetic resonance imaging and positron emission tomography (MRI-PET) system including an MRI area and a PET area.

Throughout the drawings and the detailed description, unless otherwise described or provided, the same drawing reference numerals will be understood to refer to the same elements, features, and structures. The drawings may not be to scale, and the relative size, proportions, and depiction of elements in the drawings may be exaggerated for clarity, illustration, and convenience.

DETAILED DESCRIPTION

The following detailed description is provided to assist the reader in gaining a comprehensive understanding of the methods, apparatuses, and/or systems described herein. However, various changes, modifications, and equivalents of the systems, apparatuses and/or methods described herein will be apparent to one of ordinary skill in the art. The progression of processing steps and/or operations described is an example; however, the sequence of and/or operations is not limited to that set forth herein and may be changed as is known in the art, with the exception of steps and/or operations necessarily occurring in a certain order. Also, descriptions of functions and constructions that are well known to one of ordinary skill in the art may be omitted for increased clarity and conciseness.

The features described herein may be embodied in different forms, and are not to be construed as being limited to the examples described herein. Rather, the examples described herein have been provided so that this disclosure will be thorough and complete, and will convey the full scope of the disclosure to one of ordinary skill in the art.

Magnetic resonance imaging and positron emission tomography (MRI-PET) systems will be described in detail and the thicknesses of layers or regions for the drawing figures are exaggerated for clarity.

FIG. 1 illustrates an example of an MRI-PET system 100 including an MRI areas 10 and a PET area 11. Referring to FIG. 1, the MRI-PET system 100 includes a cylindrical magnetic structure having a main magnet 101 disposed at the outermost surface of the cylindrical magnetic structure and a gradient coil assembly 102 disposed within the main magnet 101. The main magnet 101 and the gradient coil assembly 102 are sequentially arranged from the outside to the inside. As shown in FIG. 1, the MRI-PET system 100 includes a PET area 11 and MRI areas 10 disposed at both sides of the PET area 11. Each MRI area 10 includes a radio-frequency (RF) coil 104 disposed within the gradient coil assembly 102, while the PET area 11 includes a PET unit 114 disposed within the gradient coil assembly 102. The PET unit 114 is disposed within the gradient coil assembly 102 and the RF coils 104 are disposed at both sides of the PET unit 114.

A examination table 15 slides a subject 16 into a bore 13, and the bore 13 may be located within the RF coils 104 and the PET unit 114 of the MRI-PET system 100. The subject 16 is placed at a predetermined position on the examination table 15. Referring to FIG. 1, the bore 13 is formed in a z-axis direction and surrounded by the RF coils 104 and the PET unit 114, which are disposed alternately along the z-axis direction. The MRI-PET system 100 may further include a drive and control unit (not shown) for driving and controlling the main magnet 101, the gradient coil assembly 102, the PET unit 114, and the RF coils 104. After placing the subject 16 on the examination table 15, the examination table 15 is moved in the z-axis direction so that the subject 16 is slid in and is examined within the MRI-PET system 100.

While components related to the present example are illustrated in the MRI-PET system 100 of FIG. 1, it is understood that those skilled in the art may include other general components. For example, the MRI-PET system 100 may include a display (not shown). The display may be implemented as a liquid crystal display (LCD), a light-emitting diode (LED) display, a plasma display panel (PDP), a screen, a terminal, and the like. A screen may be a physical structure that includes one or more hardware components that provide the ability to render a user interface and/or receive user input. The screen can encompass any combination of display region, gesture capture region, a touch sensitive display, and/or a configurable area. The screen can be embedded in the hardware or may be an external peripheral device that may be attached and detached from the apparatus. The display may be a single-screen or a multi-screen display. A single physical screen can include multiple displays that are managed as separate logical displays permitting different content to be displayed on separate displays although part of the same physical screen.

As another example, the MRI-PET system 100 may include a user interface (not shown). The user interface may be responsible for inputting and outputting input information regarding a user and an image. The user interface may include a network module for connection to a network and a universal serial bus (USB) host module for forming a data transfer channel with a mobile storage medium, depending on a function of the MRI-PET system 100. In addition, the user interface may include an input/output device such as, for example, a mouse, a keyboard, a touch screen, a monitor, a speaker, a screen, and a software module for running the input/output device.

The main magnet 101 may be a permanent magnet or superconductive magnet having a cylindrical shape. The main magnet 101 creates a main magnetic field for magnetizing atomic nuclei of elements in the subject's body, such as hydrogen (H), phosphorous (P), and sodium (Na), which induce magnetic resonance. The gradient coil assembly 102 applies a gradient magnetic field having a predetermined slope in the nuclear spin direction to the subject 16 that is placed within a static magnetic field created by the main magnet 101. Three gradient coils may be used to create gradient magnetic fields in x-axis, y-axis, and z-axis directions. While the main magnet 101 creates a static magnetic field around the subject 16, the gradient coil assembly 102 creates a variable field, which allows different parts of the subject to be scanned.

Figure 2:
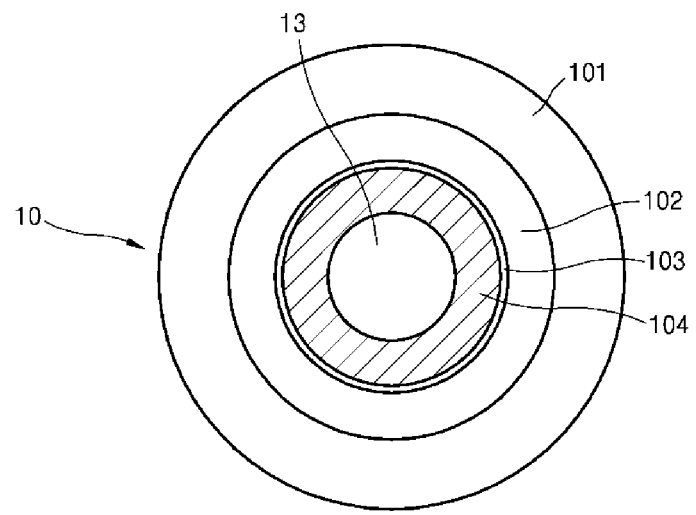
FIG. 2 illustrates an example of a cross-section of the MRI area in the MRI-PET system of FIG. 1.

FIG. 2 illustrates an example of a cross-section of the MRI area 10 in the MRI-PET system 100 of FIG. 1. Referring to FIGS. 1 and 2, the MRI area 10 may include the main magnet 101, the gradient coil assembly 102 disposed within the main magnet 101, and the RF coils 104 disposed within the gradient coil assembly 102. An RF shield 103 may be disposed between the gradient coil assembly 102 and the RF coils 104. The RF shield 103 may block the radio frequency generated by the RF coils 104.

The MRI area 10 has the RF coils 104 disposed inside the gradient coil assembly 102 to non-invasively obtain an image containing information about biological tissue and body parts of the subject 16. When a static magnetic field created by the main magnet 101 and a gradient magnetic field generated by the gradient coil assembly 102 are applied to the subject 16 within the bore 13, the RF fields produced by RF pulses from the RF coils 104 may be applied to the subject 16. Thus, the MRI area 10 receives and transmits an MRI signal generated by the subject 16. A diameter of the bore 13 may be selectively determined in accordance with inner diameters of the main magnet 101, the gradient coil assembly 102, the RF coils 104, the size of the table 15, and the desired opening of the bore 13.

Figure 3A:
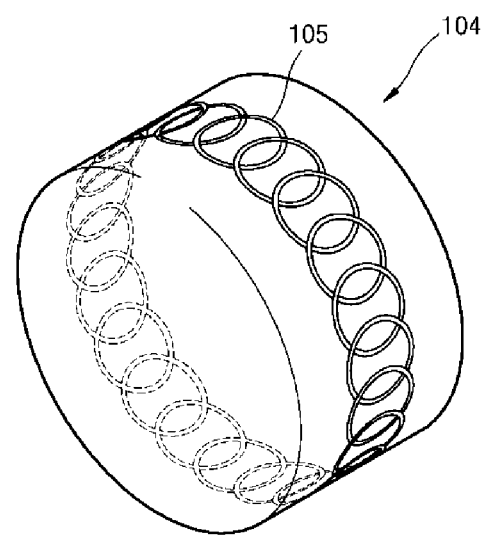
FIGS. 3A through 3C illustrate examples of a radio-frequency (RF) coil disposed in the MRI area of the MRI-PET system of FIG. 1.
Figure 3B:
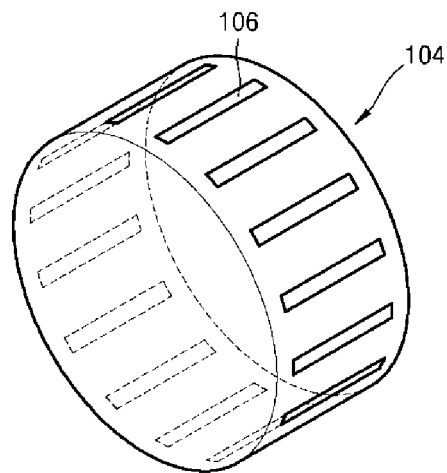
Figure 3C:
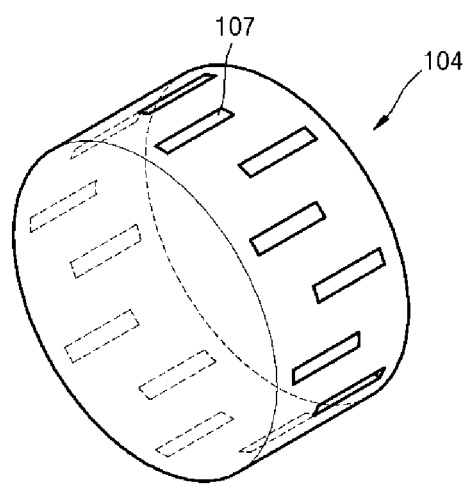

Various arrangements of the RF coil 104 may be designed and configured. For example, FIG. 3A illustrates an example of the RF coil 104 formed in an MRI area. FIGS. 3B and 3C illustrate other examples of the RF coil 104 formed in the MRI area 10.

Referring to FIG. 3A, the RF coil 104 may include a plurality of loop coils 105, which are disposed around a surface of the cylindrical RF coil 104 surrounding the bore 13. A particular RF pulse may be applied to each of the loop coils 105 to generate an RF field. Although the plurality of loop coils 105 partially overlap each other in the example shown in FIG. 3A, the loop coils 105 may be separate from each other. The arrangement and number of loop coils 105 in the RF coil 104 may be selectively adjusted. Furthermore, when the plurality of loop coils 105 partially overlap each other, each loop coil 105 may be separated from its neighboring coils by an insulator and each coil may be controlled independently.

Referring to FIGS. 3B and 3C, the RF coil 104 includes a plurality of plate coils 106 and 107 having a strip-line shape. The plate coils 106 and 107 may be arranged radially around a surface of the cylindrical RF coil 104 surrounding the bore 13. Referring to FIG. 3B, the plate coils 106 may be disposed on the surface of the RF coil 104, uniformly along the centerline of the RF coil 104. Alternatively, as shown in FIG. 3C, the plate coils 107 may be disposed on the surface of the RF coil 104 in a staggered pattern along the centerline of the RF coil 104. The arrangements of the plate coils 106 and 107 may be selectively determined. An RF field may be generated by applying a particular RF pulse to each of the plate coils 106 and 107.

The examples shown in FIGS. 3A-3C are only non-exhaustive illustrations of the RF coil 104, the loop coils 105, plate coils 106, and plate coils 107 and other shapes and configuration of the RF coil, loop coils, and plate coils are considered to be well within the scope of the present disclosure. For example, the distances between or the arrangements of the loop coils 105 and the plate coils 106 and 107 shown in FIGS. 3A through 3C may be selectively adjusted. Although FIGS. 3A through 3C show that individual coils in the RF coil 104 are loop or plate coils, the shape of the coils of the RF coil 104 are not limited to the loop and the strip-line. For example, the RF coil 104 may include some bent coils or coils with different curvature ratios, where the curvature ratios increases linearly, progressively, or less than linearly. Each of the loop coils 105 and the plate coils 106 and 107 may be independently controlled by a drive and control unit.

Figure 4A:
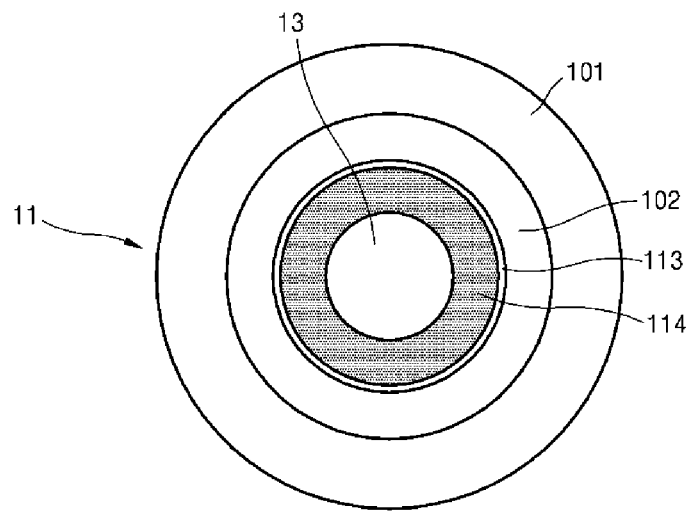
FIG. 4A illustrates an example of a cross-section of a PET area in the MRI-PET system of FIG. 1.
Figure 4B:
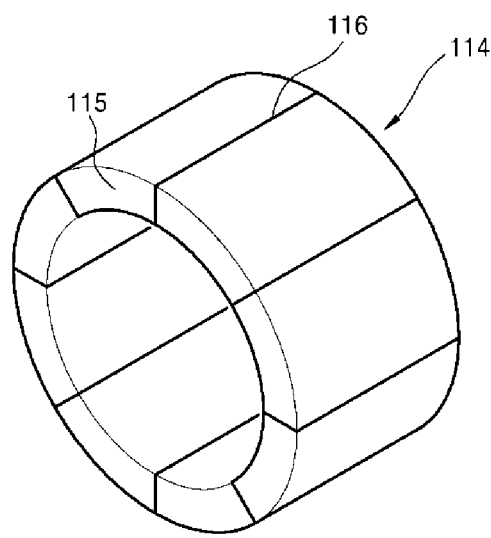
FIG. 4B illustrates an example of a PET unit in the PET area of the MRI-PET system of FIG. 1.

FIG. 4A illustrates an example of a cross-section of the PET area 11 in the MRI-PET system 100, and FIG. 4B illustrates an example of the PET unit 114 in the PET area 11. Referring to FIGS. 1, 4A, and 4B, the PET area 11 includes the main magnet 101, the gradient coil assembly 102 disposed inside the main magnet 101, and the PET unit 114 disposed inside the gradient coil assembly 102. The PET area 11 may further include an RF shield 113 that is disposed between the gradient coil assembly 102 and the PET unit 114. The RF shield 113 mayblock the RF generated by the RF coil 104 formed near the PET unit 114.

As shown in FIG. 4B, the PET unit 114 may include a plurality of PET detectors 115 arranged as an annular ring. An RF shield 116 may be selectively disposed between the PET detectors 115. The examination table 15 on which the subject 16 lies is moved into the bore 13 of the MRI-PET system 100 to reache a predetermined location. When the examination table 15 stops at the predetermined location, the PET detectors 115 surrounding the subject 16 detect gamma rays emitted from the subject 16 to obtain the desired image information.

The MRI-PET system 100 may have an integrated structure including the MRI area 10 and the PET area 11. The PET area 11 may be located independently between the MRI areas 10 to minimize interference in transmission and reception of signals between the respective devices. While FIG. 1 shows that one MRI area 10 is provided at both sides of the PET area 11, other configurations are considered to be well within the scope of the present disclosure.

In the MRI-PET system 100, the MRI area 10 and the PET area 11 may share the same main magnet 101 and the gradient coil assembly 102. The PET area 11 may include the PET unit 114 disposed radially around the bore 13 and within the cylindrical gradient coil assembly 102. The RF coils 104 may be arranged at both sides of the PET unit 114.

Figure 5:
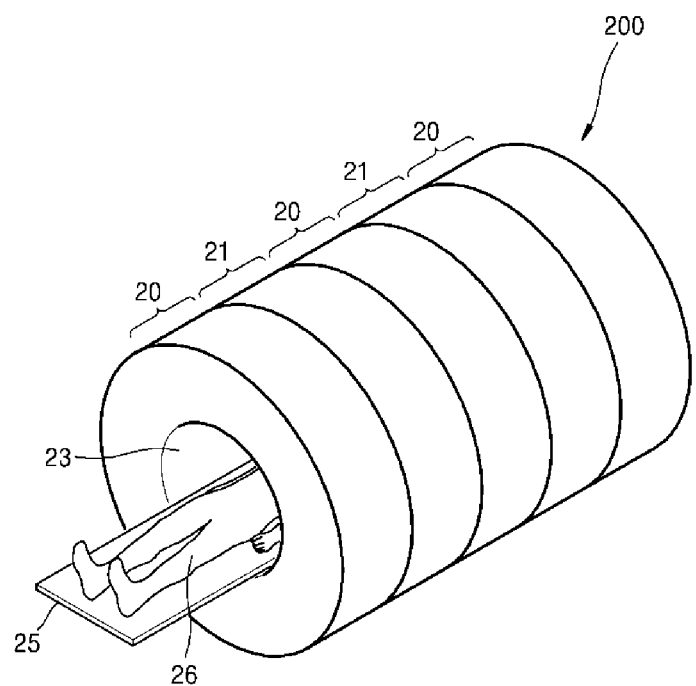
FIG. 5 illustrates another example of an MRI-PET system.

FIG. 5 illustrates another example of an MRI-PET system 200. Referring to FIG. 5, the MRI-PET system 200 includes a plurality of alternating MRI areas 20 and PET areas 21. The MRI areas 20 are disposed at the center and at the two outermost edges of the MRI-PRI system 200. The PET areas 21 are disposed between the MRI areas. RF shields may be disposed between the MRI areas 20 and the PET areas 21 and on surfaces of the MRI areas 20 and the PET areas 21. A examination table 25 slides a subject 26 into a bore 23, and the bore 13 may be located within the RF coils 104 and the PET unit 114 of the MRI-PET system 100. When the examination table 25 slides into the bore 23 with the subject 26, the MRI-PET system 200 starts the examination of the subject 26. The loop coils 105, the plate coils 106 and 107, and the PET detectors 115 shown in FIGS. 2, 3A through 3C, and 4A and 4B may also be used for configurations of the MRI areas 20 and the PET areas 21 The above descriptions of FIGS. 1-4B with respect to MRI-PET system 100 is also applicable to the analogous features of MRI-PET system 200, and is incorporated herein by reference. Thus, the above description may not be repeated here.

Figure 6:
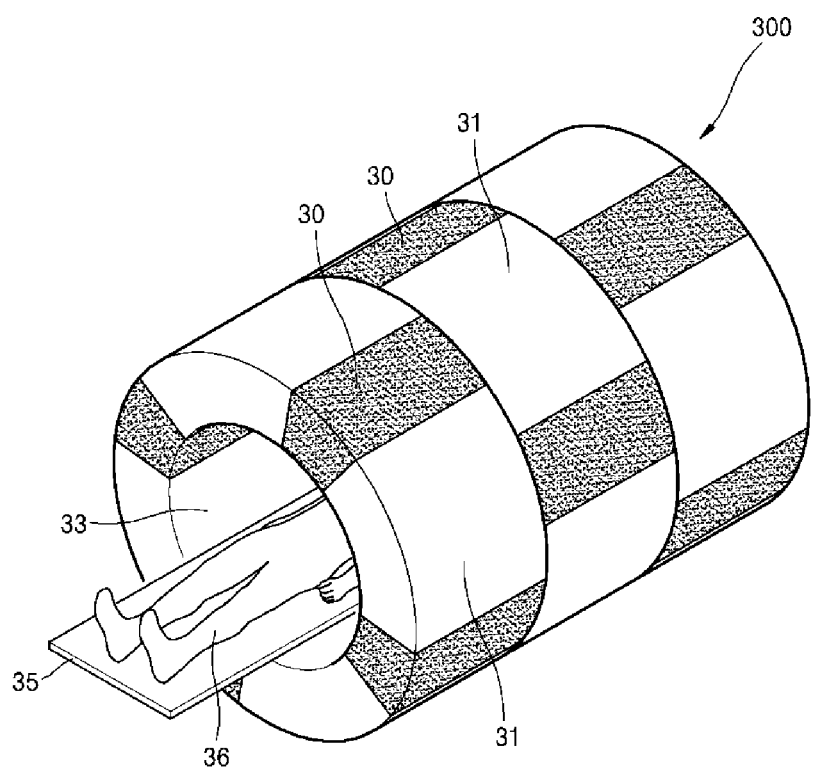
FIG. 6 illustrates yet another example of an MRI-PET system.

FIG. 6 illustrates another example of a MRI-PET system 300. Referring to FIG. 6, the RF coils 30 and PET units 31 are alternately disposed along the inner surface of the gradient coil assembly 102, which is disposed inside the main magnet 101

FIGS. 1 through 5 show that the RF coils 104 and the PET units 114 are arranged along the z-axis direction in which the bore 13, 23 is formed. The RF coils 30 and the PET units 31 are arranged alternately with each other in ring structures around the z-axis direction. RF shields may be disposed between the RF coils 30 and the PET units 31 and on surfaces of the RF coils 30 and the PET units 31 to minimize the effects of RF fields. The RF coil 30 may be configured to include individual units shown in FIGS. 3A through 3C, and the PET unit 31 may include the PET detectors 115 as shown in FIG. 4B. The above descriptions of FIGS. 1-4B with respect to MRI-PET system 100 is also applicable to the analogous features of MRI-PET system 300, and is incorporated herein by reference. Thus, the above description may not be repeated here.

According to another non-exhaustive example, the MRI-PET systems may have a PET unit separated from an MRI unit, thereby minimizing interferences in transmission and reception of signals between MRI and PET devices. Furthermore, a PET receiver and an MRI receiver with various configurations may be provided.

While this disclosure includes specific examples, it will be apparent to one of ordinary skill in the art that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. A magnetic resonance imaging and positron emission tomography (MRI-PET) apparatus comprising:
 a magnet configured to generate a static magnetic field;
 a coil assembly configured to produce a gradient magnetic field, the coil assembly being disposed inside the magnet;
 PET elements each annularly disposed around an axis and inside the coil assembly; and
 radio-frequency (RF) coils each annularly disposed around the axis and inside the coil assembly,
 wherein the RF coils are disposed alternately with the PET elements along the axis.

2. The MRI-PET apparatus of claim of claim 1, wherein each RF coil includes a plurality of loop coils.

3. The MRI-PET apparatus of claim 2, wherein the RF coil comprises:
 a cylindrical element, and the loop coils are disposed on a surface of the cylindrical element.

4. The MRI-PET apparatus of claim of claim 2, wherein each loop of the plurality of loop coils is overlapped by an adjacent loop in an annular direction.

5. The MRI-PET apparatus of claim of claim 4, wherein a plurality of insulators separate the loop coils from each other.

6. The MRI-PET apparatus of claim 1, wherein the RF coil includes a plurality of plate coils having a strip line shape.

7. The MRI-PET apparatus of claim 1, further comprising RF shields disposed between the RF coils and the PET elements.

8. The MRI-PET apparatus of claim 1, wherein each PET element includes a PET detector.

9. The MRI-PET apparatus of claim 1, wherein a bore is formed inside the PET elements and the RF coils.

10. The MRI-PET apparatus of claim 1, wherein the PET elements and the RF coils are ring-shaped.

11. The MRI-PET apparatus of claim 1, wherein:
 the PET elements and the RF coils are disposed along a cylindrical surface to form a plurality of ring-shaped elements; and
 the ring-shaped elements are disposed along a circumference of a bore formed inside the PET elements and the RF coils.

12. A magnetic resonance imaging and positron emission tomography (MRI-PET) apparatus comprising:
 a magnet configured to generate a static magnetic field;
 a coil assembly configured to produce a gradient magnetic field, the coil assembly being disposed inside the magnet;
 a ring structure surrounding a bore formed inside the coil assembly, the ring structure including radiofrequency (RF) coils and PET elements alternately arranged with each other in an annular direction; and
 a second ring structure surrounding the bore formed inside the coil assembly, the second ring structure including other RF coils and other PET elements arranged alternately with each other in an annular direction,
 wherein the RF cons of the ring structure are axially aligned with the other PET elements of the second ring structure.

13. The MRI-PET apparatus of claim 12, further comprising RF shields disposed between the RF coils and the PET elements.

14. The MRI-PET apparatus of claim 12, wherein the PET elements of the ring structure are axially aligned with the other RF coils of the second ring structure.

* * * * *